United States Patent [19]

Goralski

[11] 4,061,639

[45] Dec. 6, 1977

[54] QUINOLINESULFONYL COMPOUNDS

[75] Inventor: Christian T. Goralski, Midland, Mich.

[73] Assignee: The Dow Chemical Company, Midland, Mich.

[21] Appl. No.: 716,747

[22] Filed: Aug. 23, 1976

[51] Int. Cl.² .................... C07D 215/36; A61K 31/47
[52] U.S. Cl. ............................ 260/283 S; 260/288 R; 424/258
[58] Field of Search ............... 260/283 S, 288 R

[56] References Cited

U.S. PATENT DOCUMENTS 2,830,029   4/1958   Adams ................................ 260/2.5
3,714,206   1/1973   Huemer et al. ..................... 260/397.7

OTHER PUBLICATIONS

Chivers, Aust. J. Chem., 1975, 28(2) 413–419, (1975).
Chemical Abstracts, vol. 82, No. 19, 125,260j, (5/12/75).
Albert et al., J. Chem. Soc. 2384 (1959).
Ponci et al., Chemical Abstracts, vol. 49, 11,657b, (1955).
Claus et al., J. Prakt Chem. 40, 447, (1889).
Buchmann et al., J. Prakt Chem., 16,152, (1962).
McCasland, J. Org. Chem., II, 277–280, (1946).

*Primary Examiner*—Donald G. Daus
*Assistant Examiner*—Diana G. Rivers
*Attorney, Agent, or Firm*—Daniel DeJoseph; C. Kenneth Bjork

[57] ABSTRACT

Quinolinesulfonyl hydrazine and quinolinesulfonyl bromide compounds of the formula

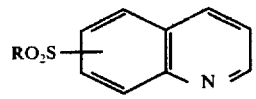

wherein R is either a bromine radical or a hydrazine radical. The quinolinesulfonyl hydrazine compounds are useful as intermediates for making quinolinesulfonyl bromide compounds, the latter being useful as antimicrobials.

1 Claim, No Drawings

QUINOLINESULFONYL COMPOUNDS

BACKGROUND OF THE INVENTION

The 5-, 6-, 7- and 8-quinolinesulfonyl chlorides are known; for example, see A. A. Albert et al., *J. Chem. Soc.*, 2384 (1959); R. Ponci et al., *Farmco* (Pavia), *Ed. Sci*, 9, 459 (1954) and *Chem. Abstr.*, 49, 11657b (1955); A. Claus et al., *J. Prakt. Chem.*, 40, 447 (1889); and G. Buchmann, et al., *J. Prakt. Chem.*, 16, 152 (1962). Their antimicrobial activity is poor.

SUMMARY OF THE INVENTION

The novel compounds of this invention are quinolinesulfonyl hydrazine and quinolinesulfonyl bromide compounds of the formula

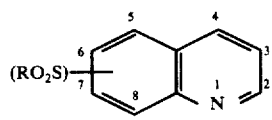

wherein R is either a bromine radical (Br—) or a hydrazine radical ($H_2NHH$—).

For convenience of description, the novel quinolinesulfonyl hydrazine compounds are herein referred to as "q. hydrazines" and the novel quinolinesulfonyl bromide compounds are herein referred to as "q. bromides".

The novel q. hydrazines consist of 5-quinolinesulfonyl hydrazine;
6-quinolinesulfonyl hydrazine;
7-quinolinesulfonyl hydrazine; and
8-quinolinesulfonyl hydrazine.

The novel q. bromides consist of
5-quinolinesulfonyl bromide;
6-quinolinesulfonyl bromide;
7-quinolinesulfonyl bromide; and
8-quinolinesulfonyl bromide.

The invention's novel compounds are crystalline solids which are of low solubility in water and of moderate solubility in many organic solvents.

The q. bromides have been found to have utility in the kill and control of bacterial and fungal organisms. The q. hydrazines have utility as intermediates for making the q. bromides.

The q. hydrazines are prepared by slowly adding substantially one molar proportion of the corresponding quinolinesulfonyl chloride (i.e. either 5-, 6-, 7- or 8-quinolinesulfonyl chloride) to substantially two molar proportions of hydrazine at about 5° C to about 15° C. The reaction is advantageously carried out in the presence of an appropriate polar organic solvent, such as, for example, methanol, ethanol or dimethylformamide as reaction medium. After the addition of the quinolinesulfonyl chloride is complete, the solution is allowed to slowly warm to room temperature to thereby precipitate the desired product, which is recovered by filtration or other conventional liquids-solids separatory techniques.

The q. bromides are prepared by slowly adding substantially four molar proportions of bromine to a solution of substantially one molar proportion of the corresponding q. hydrazine (i.e. either 5-, 6-, 7- or 8-q. hydrazine) in a suitable organic solvent, such as chloroform. Said solution should be cooled, prior to the addition of the bromine, by adding crushed ice thereto. After the addition of the bromine is complete and all of the bromine color has disappeared, the layers of the resulting slurry are separated. The organic layer is dried, such as over anhydrous magnesium sulfate. The solvent is removed, advantageously in vacuo, and the product is recrystallized from the resulting residue from an appropriate organic solvent, advantageously hexane.

The bromination of arylsulfonyl hydrazines is taught in further detail by Litvinenko et al., *Journal of the General Chemistry of the U.S.S.R.*, Vol. 34, pp. 3780–3782 (1964).

DESCRIPTION OF SOME PREFERRED EMBODIMENTS

The following examples illustrate the present invention and the manner by which it can be practiced but as such should not be construed as limitations upon the overall scope of the same. The product compounds are identified by elemental analysis and/or nuclear magnetic resonance spectroscopy.

EXAMPLE 1

Preparation of 8-Quinolinesulfonyl Bromide

A 500 ml, single-neck flask equipped with a magnetic stirrer is charged with 6.59 g (0.0295 mol) of 8-quinolinesulfonyl hydrazine and 200 ml of chloroform. Crushed ice is added, and the slurry is vigorously stirred. 9.50 g of bromine is added dropwise to the slurry with stirring. After the addition of bromine is complete and all of the bromine color has disappeared, the layers are separated. The chloroform layer is dried over anhydrous magnesium sulfate, and the chloroform is removed in vacuo leaving a pale yellow solid. The solid is slurried with hexane, filtered, and vacuum dried to give 6.00 g (0.221 mol) of 8-quinolinesulfonyl bromide m.p. 142°–144° C.

Anal. — Calcd. for 8-quinolinesulfonyl bromide ($C_9H_6BrNO_2S$): C, 39.72; H, 2.22; Br, 29.37; N, 5.14; S, 11.78. Found: C, 39.50; H, 2.30; Br, 28.80 ± 0.2; N, 5.31; S, 12.42.

The above process can be utilized to make three isomers of 8-quinolinesulfonyl bromide, namely 5-, 6- and 7-quinolinesulfonyl bromide, by employing the corresponding quinolinesulfonyl hydrazine.

EXAMPLE 2

Preparation of 8-Quinolinesulfonyl Hydrazine

A 500 ml Erlenmeyer flask equipped with a magnetic stirrer and a thermometer is charged with 200 ml of methanol and 3.40 g (0.10 mol) of 95% hydrazine. The solution is cooled to 5° C, and 11.38 g (0.05 mol) of 8-quinolinesulfonyl chloride is added in small portions at a rate such that the reaction temperature does not exceed 15° C. After the reaction is complete, the solution is allowed to warm slowly to room temperature. The precipitating solid is filtered off to give 8.00 g of 8-quinolinesulfonyl hydrazine ($C_9H_9N_3O_2S$), m.p. 135°–137° C.

Anal. — Calcd. for $C_9H_9N_3O_2S$: C, 48.42; H, 4.06; N, 18.82; S, 14.36. Found: C, 48.40; H, 4.07; N, 18.99; S, 14.30.

The above process can be utilized to make three isomers of 8-quinolinesulfonyl hydrazine, namely 5-, 6- and 7-quinolinesulfonyl hydrazine, by employing the corresponding quinolinesulfonyl chloride.

The quinolinesulfonyl bromide compounds of the invention are useful as antimicrobial agents for the control of bacteria and fungi. This is not to suggest that these compounds and mixtures thereof with usual additives are equally effective against all such organisms at the same concentration. For such uses, these compounds can be employed in an unmodified form or dispersed on a finely divided solid and employed as a dust. Such mixtures can also be dispersed in water with the aid of a surface-active agent and the resulting emulsion employed as a spray. In other procedures, the quinolinesulfonyl bromide compounds can be employed as the active constituents in solvent solutions, oil-in-water or water-in-oil emulsions. The augmented compositions are adapted to be formulated as concentrates and subsequently diluted with additional liquid or solid adjuvants to produce the ultimate treating compositions. Good results are obtained when employing compositions containing antimicrobial concentrations and usually from about 100 to about 500 parts by weight of one or more of the compounds per million parts of such compositions.

In representative activity tests, 8-quinolinesulfonyl bromide is dispersed in warm melted nutrient agar which is then poured into petri dishes and allowed to solidify, the quinoline compound being employed in an amount sufficient to provide from 10 to 500 parts by weight thereof per million parts (ppm) of the ultimate agar composition. The surface of the agar is then inoculated with a variety of bacterial and fungal pest organisms, and the inoculated plates are incubated under conditions conducive to bacterial and fungal growth. Similar check plates in which the agar contains no active quinoline or other toxic compound are similarly inoculated and incubated.

In such operations, 8-quinolinesulfonyl bromide gave 100% growth inhibition (kills) and control of the following organisms at the indicated concentrations in parts per million:

TABLE 1

| Antimicrobial Activity of 8-Quinolinesulfonyl Bromide | |
|---|---|
| Organism | Conc. in ppm |
| S. aureus | 500 |
| E. coli | 100 |
| C. albicans | 100 |
| T. mentagrophytes | 100 |
| A. niger | 100 |
| B. subtilis | 100 |
| A. aerogenes | 100 |
| C. pelliculosa | 100 |
| P. pullulans | 100 |
| S. typhosa | 100 |
| P. Str-10 | 100 |
| M. phlei | 100 |
| R. nigricans | 100 |
| C. ips | 100 |
| Trichoderm Sp. Madison P-42 | 100 |

In comparative operations, 8-quinolinesulfonyl chloride was tested for antimicrobial activity at 500 ppm using identical agar dilution tests. The following table indicates the percent growth inhibition of the following organisms:

Table 2

| Antimicrobial Activity of 8-Quinolinesulfonyl Chloride at 500 PPM | |
|---|---|
| Organism | Percent Growth Inhibition |
| S. aureus | 0 |
| E. coli | 0 |
| C. albicans | 0 |
| P. Str-10 | 0 |
| S. typhosa | 0 |
| M. phlei | 50 |
| B. subtilis | 0 |
| C. pelliculosa | 0 |
| A. aerogenes | 0 |
| P. pullulans | 0 |
| C. ips | 0 |
| Trichoderm Sp. Madison P-42 | 0 |
| R. nigricans | 0 |

What is claimed is:

1. The compound which is 8-quinolinesulfonyl bromide and which corresponds to the formula

* * * * *